(12) United States Patent
Dargam et al.

(10) Patent No.: US 11,272,900 B2
(45) Date of Patent: Mar. 15, 2022

(54) METHODS AND DEVICES FOR PROCESSING HEART SOUNDS

(71) Applicants: Valentina Dargam, Miami, FL (US); Joshua Hutcheson, Miami, FL (US)

(72) Inventors: Valentina Dargam, Miami, FL (US); Joshua Hutcheson, Miami, FL (US)

(73) Assignee: THE FLORIDA INTERNATIONAL UNIVERSITY BOARD OF TRUSTEES, Miami, FL (US)

(*) Notice: Subject to any disclaimer, the term of this patent is extended or adjusted under 35 U.S.C. 154(b) by 0 days.

(21) Appl. No.: 17/175,192

(22) Filed: Feb. 12, 2021

(65) Prior Publication Data
US 2021/0251598 A1 Aug. 19, 2021

Related U.S. Application Data

(60) Provisional application No. 62/976,584, filed on Feb. 14, 2020.

(51) Int. Cl.
A61B 5/02 (2006.01)
A61B 7/04 (2006.01)
A61B 5/00 (2006.01)

(52) U.S. Cl.
CPC ............ A61B 7/04 (2013.01); A61B 5/7257 (2013.01); A61B 5/7264 (2013.01); A61B 5/7282 (2013.01); A61B 5/742 (2013.01)

(58) Field of Classification Search
CPC ..... A61B 5/02055; A61B 5/318; A61B 5/389; A61B 5/0006
See application file for complete search history.

(56) References Cited

U.S. PATENT DOCUMENTS

2008/0001735 A1* 1/2008 Tran ................. A61B 5/7264 340/539.22
2014/0364945 A1* 12/2014 Longoria ............ A61F 2/2445 623/2.36

FOREIGN PATENT DOCUMENTS

WO WO-2004035137 A1 * 4/2004 ............. A61B 5/318

* cited by examiner

Primary Examiner — Michael J D'Abreu
(74) Attorney, Agent, or Firm — Saliwanchik, Lloyd & Eisenschenk

(57) ABSTRACT

Provided are the methods and devices to detect and quantify microstructural and functional differences in valve and cardiac disease using heart sounds, specifically for subjects suffering from early stages of valve remodeling. Such methods and devices can be used to detect and quantify microstructural and/or functional differences in, for example, aortic valves of subjects having bicuspid aortic valves and/or suffering from early Calcific Aortic Valve Disease (CAVD).

8 Claims, 10 Drawing Sheets

METHODS AND DEVICES FOR PROCESSING HEART SOUNDS

CROSS-REFERENCE TO RELATED APPLICATION

This application claims the benefit of U.S. Provisional Application Ser. No. 62/976,584, filed Feb. 14, 2020, which is hereby incorporated by reference herein in its entirety, including any figures, tables, and drawings.

BACKGROUND

Aortic Valve Disease (AVD) occurs when extracellular matrix (ECM) remodeling and calcium minerals hinder biomechanical function of aortic valve leaflets. This causes increased myocardial stress and can lead to heart failure. Aortic valve sclerosis is a thickening of the aortic valve leaflets and the formation of calcium nodules near the aortic cusps. Aortic valve stenosis occurs when large nodular calcific masses interfere with blood distribution from the heart to systemic circulation. No diagnostic strategy exists to identify patients with early aortic valve remodeling and aortic valve replacement is currently the only clinical intervention option.

AVD most commonly affects patients with congenital bicuspid aortic valve disease and elderly patients with moderate-to-severe valvular remodeling. Approximately 2.5 million people are affected with AVD, and clinical options are limited even though mechanistic studies have identified potential therapeutic targets. Underrepresented minorities in the US have an elevated risk for developing heart disease, and they undergo aortic valve replacement less frequently, leading to increased mortality. Patients with AVD are most often discovered in irreversible late stages of remodeling, where valve function is severely compromised and the only clinical intervention available is aortic valve replacement. Early detection of aortic valve remodeling could facilitate the utilization of non-invasive therapeutic strategies to target cellular changes prior to irreversible gross remodeling. Current modalities to diagnose AVD rely on complex and costly imaging techniques. However, patients are generally asymptomatic during early AVD when the remodeling may be treatable. It is unlikely that asymptomatic patients will be referred for these expensive imaging procedures.

BRIEF DESCRIPTION

In view of the challenges discussed above, there is a need in the art for methods and devices for early detection of aortic valve remodeling to therapeutically target cellular changes that occur prior to the gross remodeling observed in irreversible late stages of Aortic Valve Disease (AVD). Embodiments of the subject invention provide methods, systems, and devices to detect and quantify microstructural changes in aortic valves of subjects who have (or may have) bicuspid aortic valves and/or who are suffering (or may be suffering) from early AVD. A method can comprise processing at least one heart sound signal (for example, measuring a heart sound using a phonocardiogram recording device), segmenting the at least one heart sound into a plurality of segments, and extracting acoustic features from the plurality of segments. The acoustic features extracted can include, but are not limited to, temporal and spectral features such as dominant frequency and power spectral density. The method can further comprise administering to a subject an anti-remodeling therapy if the acoustic features extracted from a phonocardiogram recording of the subject fulfill the criteria of structural heart valve remodeling and/or have changed from a previous acoustic feature recording, such as to indicate that a structural heart valve remodeling has occurred.

In an embodiment, a system for processing at least one heart sound signal can comprise: a phonocardiogram recording device configured to record a phonocardiogram; a processor in operable communication with the phonocardiogram recording device; an optional display configured to display results of the processing of the at least one heart sound signal; and a machine-readable medium in operable communication with the processor and the phonocardiogram recording device, the machine-readable medium having instructions stored thereon that, when executed by the processor, perform the following steps: measuring, using the phonocardiogram recording device, the at least one heart sound signal to give the phonocardiogram; segmenting the at least one heart sound signal into a plurality of segments; extracting acoustic features from the plurality of segments; and performing an unsupervised machine learning process to group the at least one heart sound according to a disease stage. The processor, the machine-readable medium, and/or the display can be integrated into the phonocardiogram recording device, and/or the phonocardiogram recording device can be wearable by a subject. The segmenting of the at least one heart sound signal can comprise: selecting a region of interest (ROI) from the phonocardiogram; calculating, by the processor, a sum of squares error between envelopes of the ROI and remaining sound signals recorded in the phonocardiogram; and selecting a location of a cardiac cycle present in the at least one heart sound signal. The extracting of acoustic features can at least one of: measuring temporal and spectral features of the plurality of segments in real time; measuring frequencies of the plurality of segments and calculating a dominant frequency of the plurality of segments using at least one of Fast Fourier Transform and Short-Time Fourier Transform; measuring a power spectral density of the plurality of segments; measuring an amplitude and a shape of the power spectral density of the plurality of segments; measuring an area under a curve for the power spectral density of the plurality of segments; and identifying eigenvalues of the at least one heart sound signal using eigenvectors determined by principal component analysis of an entire heart sound database. The system can further comprise a treatment system comprising at least one reservoir and an administration device configured to administer at least one compound from the at least one reservoir to a subject when the area under the curve is below or above a predetermined value. The performing of the unsupervised machine learning process to group the at least one heart sound according to the disease stage can comprise at least one of: clustering eigenvalues for a corresponding number of eigenvectors using a k-means clustering algorithm; and correlating heart sound features of the at least one heart sound as determined in temporal, frequency, and unsupervised learning analyses to stages of disease as measured by cardiac echocardiogram parameters and tissue properties.

In another embodiment, a method for processing at least one heart sound signal can comprise: measuring, using a phonocardiogram recording device, at least one heart sound signal to give a phonocardiogram; segmenting (e.g., by a processor in operable communication with the phonocardiogram recording device) the at least one heart sound signal into a plurality of segments; and extracting (e.g., by the processor) acoustic features from the plurality of segments; and performing (e.g., by the processor) an unsupervised machine learning process to group the at least one heart sound according to a disease stage. The segmenting of the at least one heart sound signal can comprise: selecting (e.g., by the processor) a region of interest (ROI) from the phonocardiogram; calculating (e.g., by the processor) a sum of squares error between envelopes of the ROI and remaining sound signals recorded in the phonocardiogram; and selecting (e.g., by the processor) a location of a cardiac cycle present in the at least one heart sound signal. The extracting of acoustic features can at least one of: measuring temporal and spectral features of the plurality of segments in real time; measuring frequencies of the plurality of segments and calculating a dominant frequency of the plurality of segments using at least one of Fast Fourier Transform and Short-Time Fourier Transform; measuring a power spectral density of the plurality of segments; measuring an amplitude and a shape of the power spectral density of the plurality of segments; measuring an area under a curve for the power spectral density of the plurality of segments; and identifying eigenvalues of the at least one heart sound signal using eigenvectors determined by principal component analysis of an entire heart sound database. The performing of the unsupervised machine learning process to group the at least one heart sound according to the disease stage can comprise at least one of: clustering eigenvalues for a corresponding number of eigenvectors using a k-means clustering algorithm; and correlating heart sound features of the at least one heart sound as determined in temporal, frequency, and unsupervised learning analyses to stages of disease as measured by cardiac echocardiogram parameters and tissue properties. The method can further comprise administering to a subject, from which the at least one heart sound signal is measured, an anti-remodeling therapy if at least one acoustic feature of the at least one heart sound signal deviates from a respective predetermined acoustic feature value. The anti-remodeling therapy can comprise at least one of: an angiotensin-converting enzyme inhibitor; an angiotensin-converting enzyme blocker; an IL-6 antibody; a small molecule ACE inhibitor; a small molecule IL-6 inhibitor; an inhibitor of metalloproteinases; an inhibitors of leukotriene B4; an inhibitor of TGF-beta1; an inhibitor of cytokines; TGF-$\beta$1; IL-10; INF-$\gamma$; INF-$\lambda$; and a nonsteroidal anti-inflammatory drug (NSAID).

BRIEF DESCRIPTION OF DRAWINGS

FIG. 5A shows a spectrogram at week 0; FIG. 5B shows a spectrogram at week 20; and FIG. 5C shows the area under the curve for the amplitude spectrum for frequencies above 500 Hz for weeks 0, 10, and 20.

DETAILED DESCRIPTION

Figure 1:
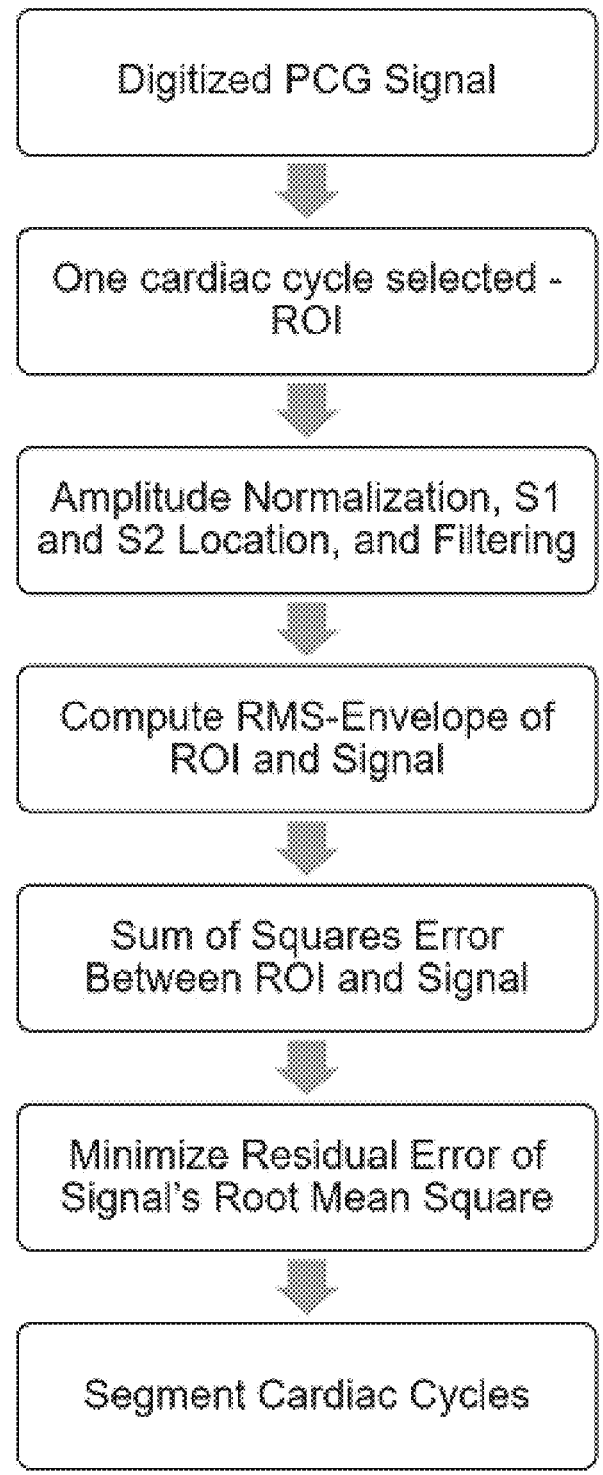
FIG. 1 shows a flowchart of a cardiac cycle segmentation method, according to an embodiment of the subject invention.
Figure 2:
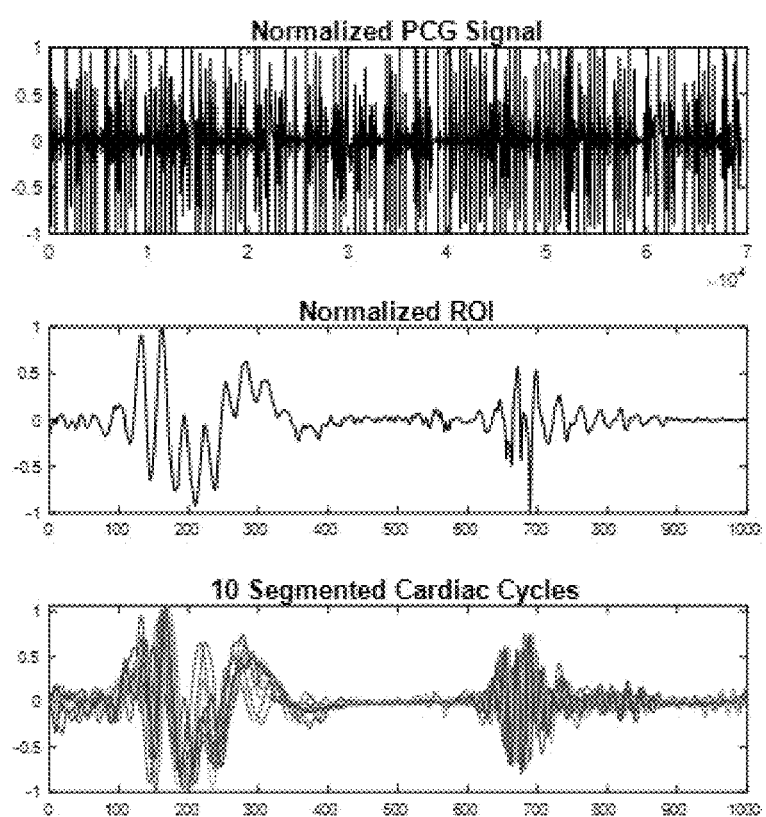
FIG. 2 shows an example of a normalized PCG signal, a normalized region of interest, and ten segmented cardiac cycles using the Sum of Squares (SSE) method, according to an embodiment of the subject invention.
Figure 3:
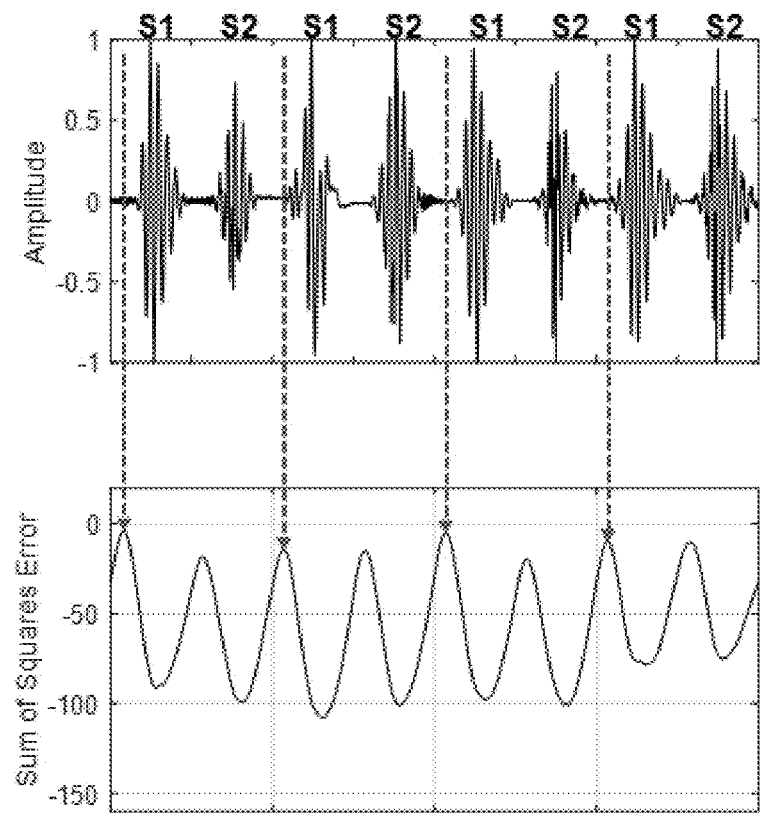
FIG. 3 shows an example of the SSE method that is used to identify the location of other cardiac cycles, according to an embodiment of the subject invention.
Figure 4:
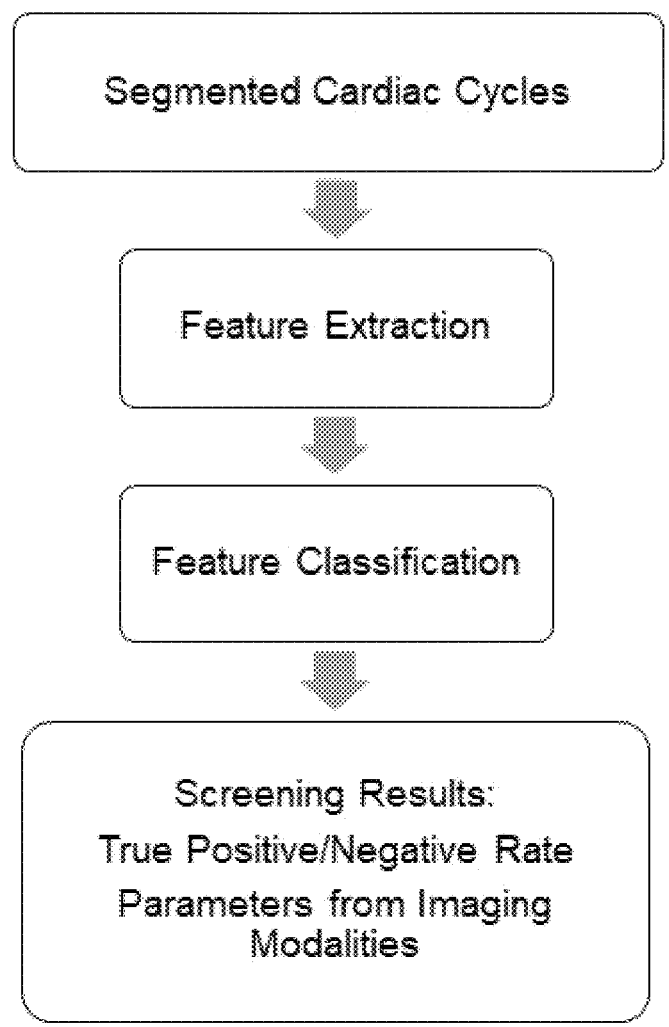
FIG. 4 shows a flowchart of the steps performed in the classification of heart sounds, according to an embodiment of the subject invention.
Figure 5A:
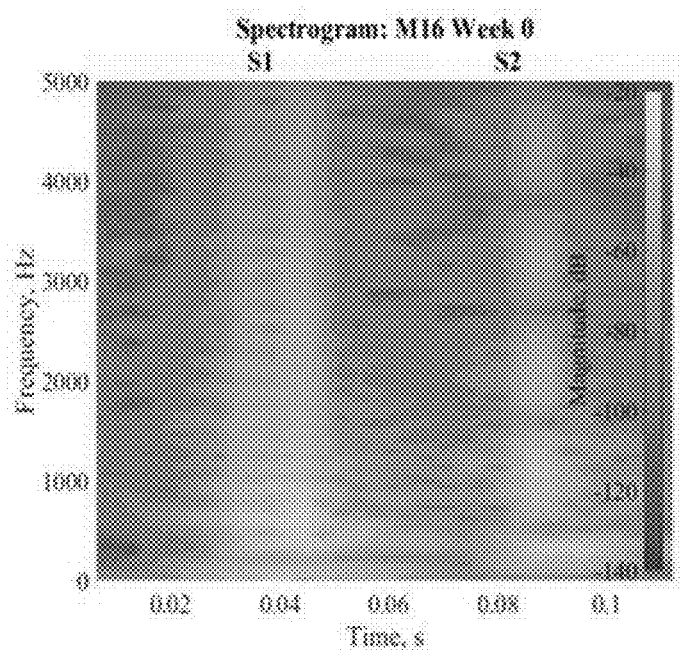
FIGS. 5A-5C show examples of spectrograms of mice during consecutive time periods following an atherogenic diet.
Figure 5B:
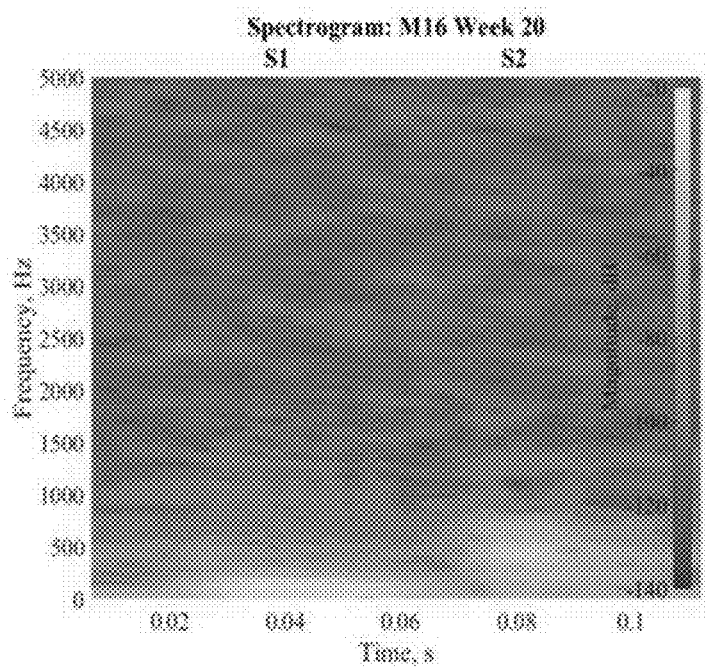
Figure 5C:
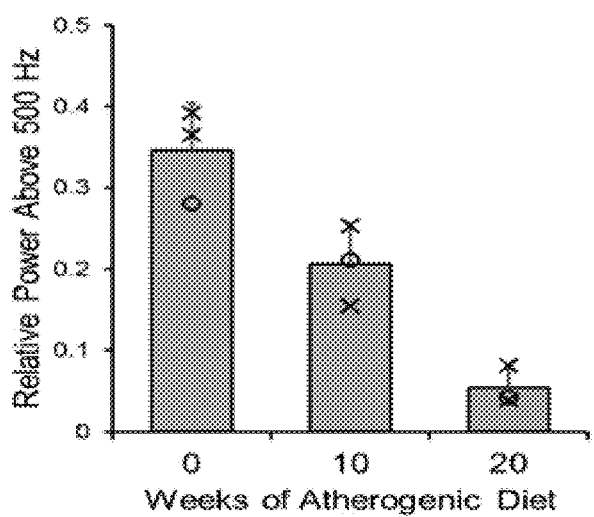
Figure 6A:
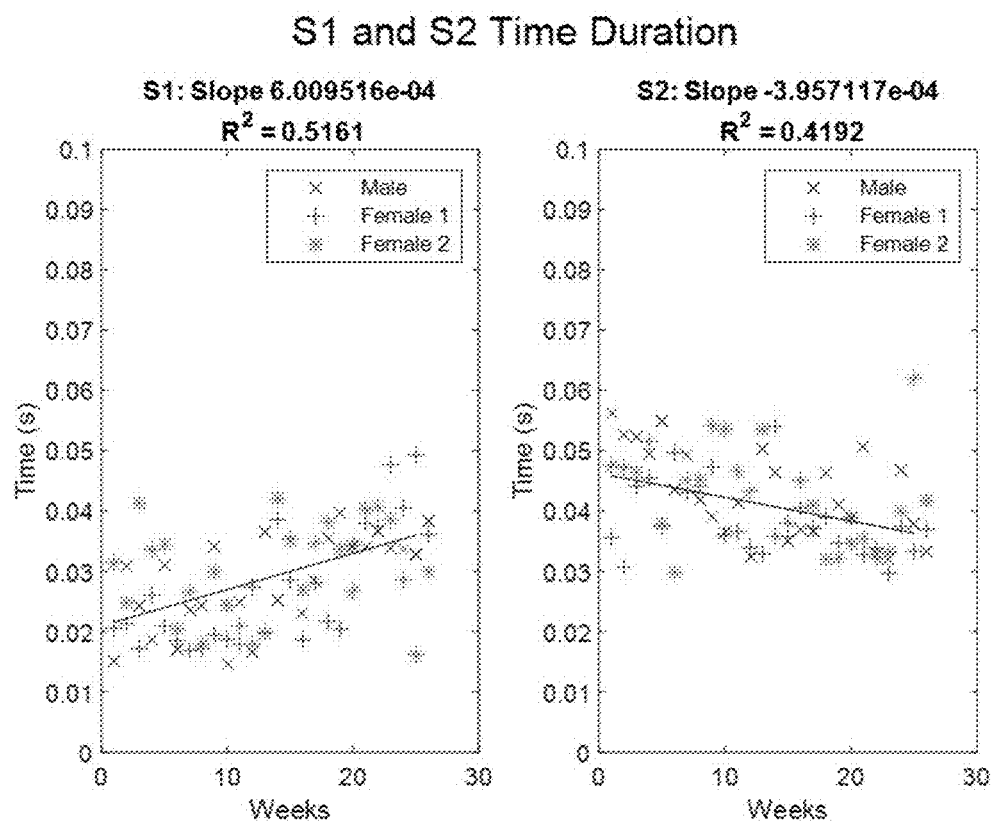
FIG. 6A shows the S1 and S2 time durations in one male and two female subjects over time where the S1 duration increases and the S2 duration decreases.
Figure 6B:
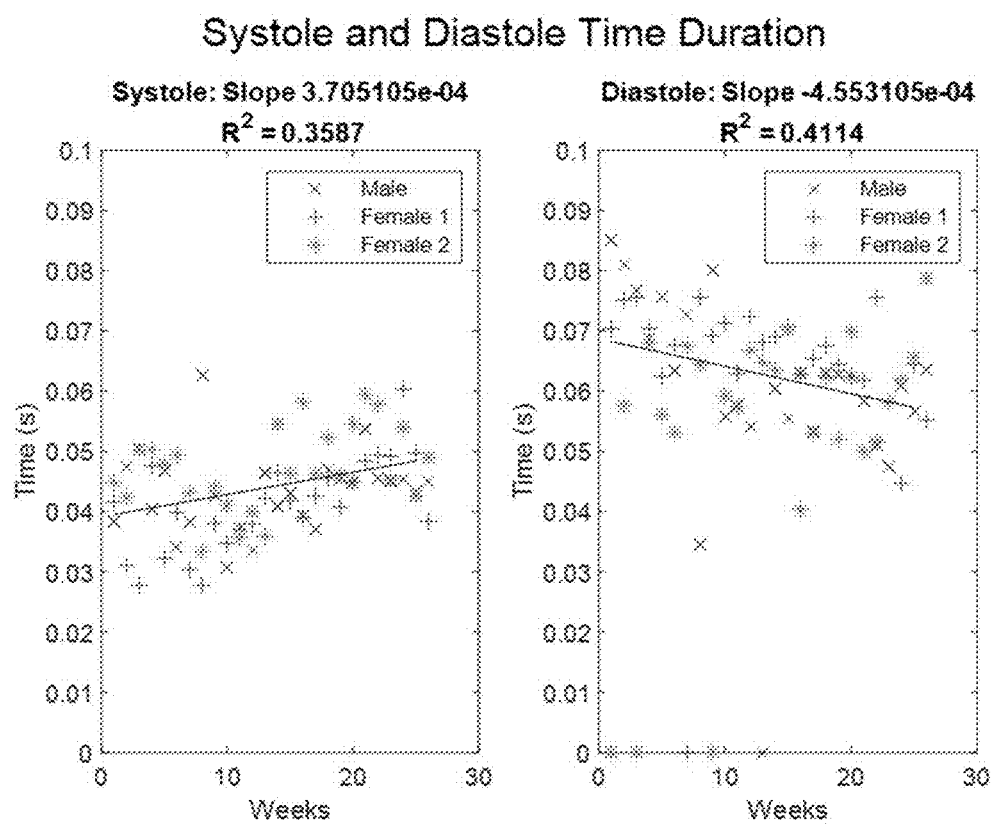
FIG. 6B shows the systole and diastole time durations in one male and two female subjects over time where the systole duration increases and the diastole duration decreases.
Figure 7:
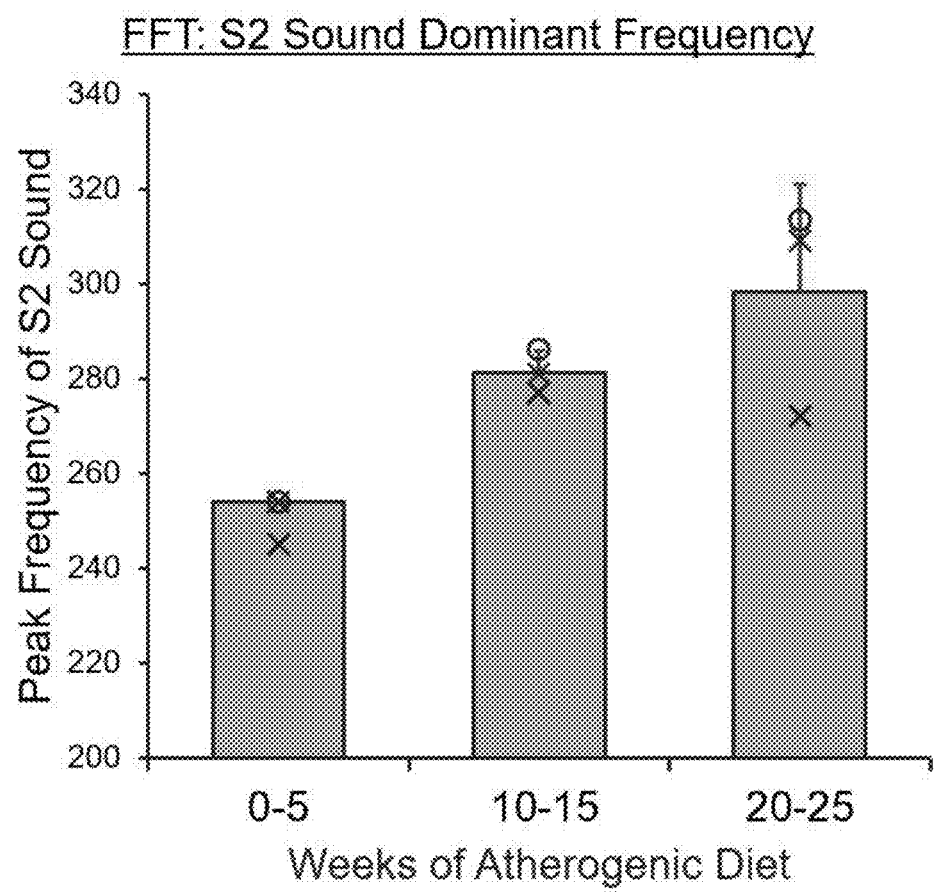
FIG. 7 shows the changes of the S2 dominant frequency over time in mice fed an atherogenic diet quantified by the average peak of the dominant S2 frequency.

Embodiments of the subject invention provide methods, systems, and devices to detect and quantify microstructural changes in aortic valves of subjects who have (or may have) bicuspid aortic valves and/or who are suffering (or may be suffering) from early Aortic Valve Disease (AVD). A method can comprise processing at least one heart sound signal (for example, measuring a heart sound using a phonocardiogram recording device), segmenting the at least one heart sound into a plurality of segments, and extracting acoustic features from the plurality of segments. The acoustic features extracted can include, but are not limited to, temporal and spectral features such as dominant frequency, power spectral density, and unsupervised machine learning methods (e.g., k-means clustering, principal component analysis). The method can further comprise administering to a subject an anti-remodeling therapy if the acoustic features extracted from a phonocardiogram recording of the subject fulfill the criteria of structural heart valve remodeling and/or have changed from a previous acoustic feature recording, such as to indicate that a structural heart valve remodeling has occurred.

Embodiments of the subject invention provide methods and devices for the processing of heart sounds to detect and quantify early heart valve remodeling and treat a subject suffering from heart valve remodeling. The methods and devices of embodiments of the invention enable low-cost monitoring of heart valve physiology and pathology and provide important clinical tools for non-invasive heart valve evaluations during routine physical check-ups and the assessment of treatment success of remodeling therapies. In addition, the methods and devices of the invention can be used in clinical and scientific research applications to develop and assess novel therapeutic strategies that target cellular changes of heart valves that, so far, have been impossible to detect non-invasively. Specifically, the methods and devices of embodiments of the invention detect structural changes of heart valve by quantifying acoustic changes prior to irreversible structural changes. This can enable new and earlier intervention strategies to prevent and/or treat heart valve structural changes.

The sound signals generated by the heart are based on distinct structural elements of the heart and coincide with specific phases of the heart electrical depolarization and contraction cycle. Each cardiac cycle is composed of four heart sounds (S1, S2, S3, S4), wherein S1 and S2 are the primary normal heart sounds. The first heart sound (S1) coincides with the "R" segment of the electrocardiogram (ECG) and depolarization and contraction of the left and right ventricles, which contractions move the blood inside the ventricles and effectuate the closing of the mitral valve and the tricuspid valves. The second heart sound (S2) coincides with the "T" segment of the ECG, relaxation of the ventricles and the closure of the aortic and pulmonary valves. Although not necessarily present in healthy individuals, the third and fourth heart sounds coincide with fast ventricular filing in the diastole and atrial depolarization, the "P" segment of the ECG, and atrial contraction that moves blood into an expanded ventricle.

The second heart sound (S2), composed of audible frequencies heard through a stethoscope, predominantly occurs from the closure of the aortic valve where extracellular matrix (ECM) components have been hypothesized to control vibrations within the aortic leaflets.

In some embodiments of the invention, microstructural changes in heart valves are identified and quantified my measuring changes in the acoustic frequencies and frequency characteristics of heart sounds.

The methods and devices of embodiments of the invention can be used on aortic and pulmonary valves and on mitral and tricuspid valves. Advantageously, by placing the recording device over the chest portion that is closest to the respective heart valve, distinct frequency components that are generated by the heart valve of interest can be recorded.

In some embodiments, changes in aortic valve structure are identified and quantified by measuring changes in the aortic valve acoustic frequency (S2 sound) response. In other embodiments, changes in pulmonary valve structure are identified and quantified by measuring changes in the pulmonary valve acoustic frequency (S2 sound) response. The measurements of the acoustic frequency response of the S2 sound are measured at the chest surface position where the aortic valve sound is detected during routine auscultation for measuring changes in the aortic valve and the at the chest position where the pulmonary valve sound is detected during routine auscultation for measuring changes in the pulmonary valve.

In further embodiments, changes in mitral valve structure are identified and quantified by measuring changes in the mitral valve acoustic frequency (S1 sound) response. In other embodiments, changes in tricuspid valve structure are identified and quantified by measuring changes in the tricuspid valve acoustic frequency (S1 sound) response. The measurements of the acoustic frequency response of the S1 sound are measured at the chest surface position where the mitral valve sound is detected during routine auscultation for measuring changes in the mitral valve and the at the chest position where the tricuspid valve sound is detected during routine auscultation for measuring changes in the tricuspid valve.

Using the methods and devices of embodiments of the invention heart sound signals obtained from a digital stethoscope are recorded, quantified, the frequency components of the signals analyzed and the different stages of heart valve structural changes such as remodeling quantified.

In other embodiments, the methods and devices can be used detect and quantify structural and microstructural changes at the vocal cords of a subject. In these embodiments, sound signal recording accords over the neck and the frequency components of predetermined vocal sounds are recorded and quantified.

In further embodiments, the methods and devices can be used to detect and quantify blood flow turbulences in arteries in the body of a subject by recording a sound at the body surface overlaying the artery, where the sound is created by blood flow turbulences.

In yet further embodiments, the methods and devices can be inserted into a body cavity or, during surgery, into a body and sounds recorded from an adjacent vessel to detect and quantify flow turbulences and detect and quantify vessel wall structural and microstructural changes.

Any sound recording device or machine can be used in the methods of embodiments of the invention and in connection with the devices of the invention. Commercially available devices that are useful in the context of embodiments of the subject invention include, but are not limited to, digital stethoscopes.

In a first step of a heart sound analysis according to embodiments of the invention, the cardiac cycles are segmented from all other sounds in a sound recording. Heart sound segmentation is necessary to analyze time and frequency characteristics of multiple S1 and S2 sounds and allow statistical analysis and quantification of sound characteristics that coincide with structural characteristics of the heart valves.

In embodiments of the invention, a phonocardiogram (PCG) signal is recorded using a digital stethoscope and a novel segmentation method is applied to the PCG recorded signal to localize the heart sounds in the PCG using a sum of squares error. In some embodiments, a region of interest (ROI) in the PCG is selected. The signal's envelope is calculated for both the ROI and the remaining PCG signals, that is the PCG signals outside the ROI. In preferred embodiments, a sum of squares error is calculated between the envelope of the ROI and the remaining PCG signals. In preferred embodiments, the ROI is a single cardiac cycle. In further preferred embodiments, the lowest error in the calculated sum of squares error is selected as the location of other cardiac cycle's heart sounds.

Figure 8:
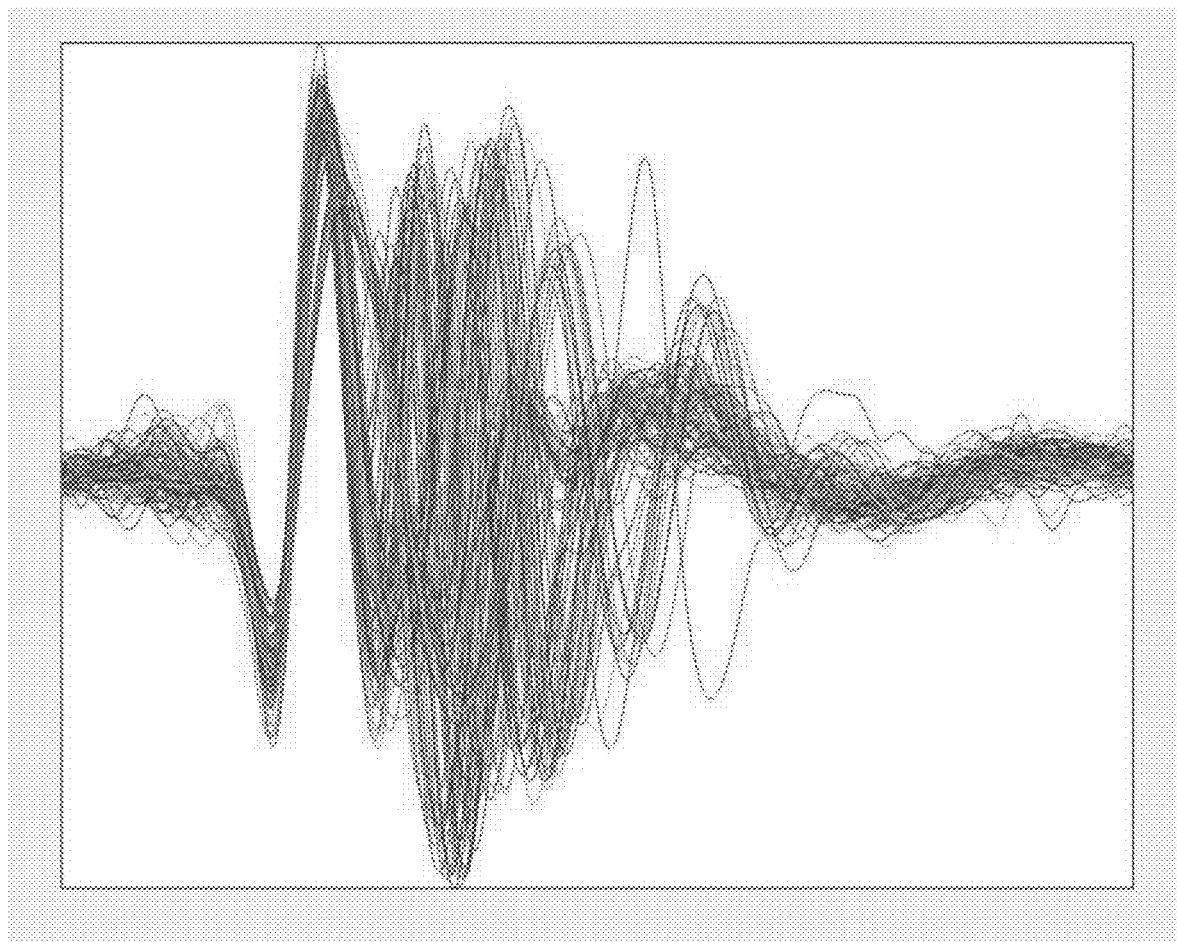
FIG. 8 shows an example of S2 heart sounds aligned in the time domain after identifying the location of S2 start using the region of interest and sum of the residual error methodology described herein.

Heart sounds (S1 or S2) and/or a heart sound cycle (S1+S2) of interest can be further aligned by identifying and/or detecting the changes in the root-mean square of the signal that minimizes the sum of the residual error of each ROI, which can be any individual sound (S1 or S2) or cycle (S1+S2). This ensures that the sound is aligned at the start of the sound in the time domain (see FIG. 8).

After the sounds S1 and S2 have been localized in a PCG recording, features of the acoustic signals are extracted. The features to be extracted include, but are not limited to, temporal and spectral characteristics.

In preferred embodiments the dominant frequency components of S1 and S2 are extracted using Fast Fourier Transform (FFT) and Short-Time Fourier Transform (STFT) methods. In other embodiments, the power spectral density and its amplitude and shape (full-width half-max lengths) for each heart sound S1 and S2 are extracted. In further embodiments, the intensities of S1 and S2 sounds are calculated by Short-Time Fourier Transform. In yet other embodiments, the duration of S1 and S2 sounds and the duration of diastole and systole of a cardiac cycle are calculated. In preferred embodiments, the presence of high frequency components is measured using Fast Transform Fourier and Short-Time Fourier Transform. In some embodiments, principal component analysis is performed to measure the principal components of the heart sounds in the time and frequency domains. In some embodiments the ratio of systole time to diastole time is extracted. In further embodiments, characteristics from at least one heart signal's envelope and entropy are extracted.

In preferred embodiments, the average dominant frequency for the S2 sound is calculated and a structural change in an aortic valve quantified according to an increase in dominant frequency as measured compared to a predetermined dominant frequency value and/or to a dominant frequency previously measured in the subject.

In further embodiments, the duration of S1 and S2 sounds are measured and a structural change in an aortic valve is quantified according to an increase in the duration of S1 and a decrease in the duration of S2.

In yet further embodiments, the duration of systole and diastole are measured and a structural change in an aortic valve is quantified according to an increase in the duration of the systole and a decrease in the duration of the diastole.

The extracted sound features are also compared to a database of heart sound features with classified pathological conditions.

In preferred embodiments of the invention, a method for processing at least one heart sound signal is provided, the method comprising the steps of measuring, using a phonocardiogram recording device, at least one heart sound signal; segmenting the at least one heart sound signal into a plurality of segments; and extracting acoustic features from the plurality of segments.

In further embodiments, the segmenting comprises selecting a region of interest (ROI) from the phonocardiogram; calculating, by a processor in operable communication with the phonocardiogram recording device, a sum of squares error between the envelopes of the ROI and the remaining sound signals recorded in the phonocardiogram; and selecting the location of other cardiac cycles.

In further embodiments, the extracting comprises measuring temporal and spectral features of the plurality of segments in real time. In yet further embodiments, the extracting further comprises measuring frequencies of the plurality of segments and calculating a dominant frequency of the plurality of segments using Fast Fourier Transform and Short-Time Fourier Transform. In other embodiments, the extracting further comprises measuring a power spectral density of the plurality of segments and further measuring a amplitude and a shape of the power spectral density of the plurality of segments.

In order to extract more temporal characteristics of the acoustic signal, unsupervised machine learning methods can be applied. Principal component and cluster analysis can be applied to group data according to the absence or stages of a disease. Principal component analysis (PCA) of the normalized heart sounds can identify the direction vectors with the most variance of the data. Vectors from PCA are the eigenvectors of the covariance matrix scaled by the square root of the corresponding eigenvalues of the signal, or scores. Each vector is associated with a principal component (PC), and a score gives the variance from the PC's vector for each heart sound cycle or individual sound. Eigenvectors are determined by running PCA on the entire dataset, which can be individual sounds (S1 or S2) or cardiac cycles (S1+S2). For each heart sound or cycle, the eigenvalues are used to classify heart sound characteristics according to the labels of disease stage, which is measured by echocardiogram disease parameters and/or tissue characteristics. The eigenvalues can be used for k-means clustering analysis, which identifies clusters of the data in the PC space. The optimal number of PCs and clusters can be identified so that they are classified correctly according to their disease label.

Also provided is a processing system for processing at least one heart sound signal, the system comprising: a phonocardiogram recording device for recording a phonocardiogram; a processing device comprising a processor and internal or external memory, wherein the processor is in operable communication with the phonocardiogram and is configured to calculate the sum of squares error between the envelope of a region of interest of a phonocardiogram and the envelope of the remaining sound signals recorded in the phonocardiogram; segment the phonocardiogram signal into heart sound segments, wherein other cardiac cycles are located in regions of the lowest error; calculate a power spectrum for each heart sound segment and an area under the curve for the power spectrum; and a display displaying a signal when the area under the curve of at least one power spectrum is below or above a predetermined value.

In some embodiments, the processing device and the display are integrated into the phonocardiogram recording device.

In further embodiments, the processing system is wearable by a subject and can be used to measure changes in heart sound frequency characteristics during, e.g., anti-remodeling therapy and measure the success of the therapy, or lack thereof.

In some embodiments, the processing system further comprises a treatment system. In some embodiments, the treatment system comprises at least one reservoir and an administration device. In some embodiments, the administration device is configured to administer a compound from the at least one reservoir to the subject, wherein the administration is initiated through the processor of the processing system at the occurrence of a predetermined event.

In preferred embodiments, the predetermined event is based on an area under the curve of a power spectrum calculated by the processing device from the sounds recorded using the phonocardiogram recording device. In some embodiments, the area under the curve of at least one power spectrum is calculated and the predetermined event is a value of the area under the curve of the at least one power spectrum, which value is below or above a predetermined value.

In other embodiments, the predetermined event is a value of the area under the curve of at least one power spectrum, which value is different from a value recorded previously in the subject. In some embodiments, the value of the area under the curve calculated is below a value of the area under the curve previously recorded. In other embodiments, the value of the area under the curve is above a predetermined value of the area under the curve or a previously recorded value under the curve of the at least one power spectrum.

Also provided is a method for detecting and treating a heart valve remodeling in a subject, the method comprising: measuring, using a phonocardiogram recording device, at least one heart sound signal; segmenting the at least one heart sound signal into a plurality of segments; extracting acoustic features from the plurality of segments; and administering to the subject an anti-remodeling therapy if at least one acoustic feature deviates from a predetermined acoustic feature value.

In some embodiments, the segmenting step of the method comprises: selecting a region of interest (ROI) from the phonocardiogram; calculating, by a processor in operable communication with the phonocardiogram recording device, a sum of squares error between the envelopes of the ROI and the remaining sound signals recorded in the phonocardiogram; and selecting the location of other cardiac cycles.

In some embodiments, the extracting step of the method comprises measuring temporal and spectral features of the plurality of segments in real time.

In some embodiments, the extracting step further comprises measuring frequencies of the plurality of segments and calculating a dominant frequency of the plurality of segments using Fast Fourier Transform and Short-Time Fourier Transform and the anti-remodeling therapy is administering if the dominant frequency is below or above a predetermined value.

In some embodiments, the extracting step further comprises measuring a power spectral density of the plurality of segments and measuring a amplitude and a shape of the power spectral density of the plurality of segments.

In preferred embodiments, the extracting step of the method further comprises calculating from the spectral features of the plurality of the segments a power spectrum and calculating from the power spectrum an area under the curve, and wherein the anti-remodeling therapy is administered if the area under the curve is below or above a predetermined value.

In further preferred embodiments, the anti-remodeling therapy includes, but is not limited to, an angiotensin-converting enzyme inhibitor, an angiotensin-converting enzyme blocker, an IL-6 antibody, a small molecule ACE inhibitor, a small molecule IL-6 inhibitor, inhibitors of metalloproteinases, inhibitors of leukotriene B4, inhibitors of TGF-beta1, and other cytokine inhibitors. Any anti-remodeling therapy known in the art can be used in the methods and devices of embodiments of the subject invention.

In some embodiments, the methods and devices are used to measure heart sound frequency characteristics and administer other therapies based on the heart sound frequency characteristics. In some embodiments, the method comprises the step of calculating from the spectral features of the plurality of segments a power spectrum and calculating from the power spectrum an area under the curve, wherein the therapy is administered if the area under the curve deviates from a predetermined value.

In some embodiments, the therapy is administered if the area under the curve is below a predetermined value and/or a previously recorded value. In other embodiments, the therapy is administered if the area under the curve is above a predetermined value and/or a previously recorded value.

The therapies to be administered include, but are not limited to, anti-inflammatory agents, immunosuppressive agents, and agents that recruit immune cells of interest and cytokines that are useful in the therapy of a heart valve condition, a structural heart valve change and/or a structural change in a body vessel, including an artery.

Therapeutic agents can be hydrophilic or hydrophobic substances. In some embodiments, the immunomodulatory agent used in therapy of the subject include, but are not limited to, vitamin D3, vitamin D3 analogs, glucocorticoids, estrogens, rapamycin, and retinoic acid.

In some embodiments, anti-inflammatory or immunosuppressive agents that can be useful also include TGF-β1, IL-10, INF-γ and INF-λ and nonsteroidal anti-inflammatory drugs (NSAIDs) such as aspirin, ibuprofen; naproxen, triterpinoids such as betulinic acid, bardoxolone methyl, and triterpenoid saponins.

The therapies used in embodiments of the invention can be administered in a single dose or in more than one dose over a period of time to confer the desired effect. In preferred embodiments, the therapies can be formulated for parenteral administration. The therapies can be administered as part of a composition. Typically, such compositions can be prepared as injectables, either as liquid solutions or suspensions; solid forms suitable for using to prepare solutions or suspensions upon the addition of a liquid prior to injection can also be prepared; and the preparations can also be emulsified.

The compositions can be pharmaceutical forms suitable for injectable use include sterile aqueous solutions or dispersions; and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi.

Sterile injectable solutions are prepared by incorporating the active compounds in the required amount in the appropriate solvent followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum drying and freeze-drying techniques, which yield a powder of the active ingredient, plus any additional desired ingredient from a previously sterile-filtered solution thereof.

The compositions of embodiments of the subject invention can be administered to the subject being treated by standard routes, including the topical, transdermal, intraarticular, parenteral (e.g., intravenous, intraperitoneal, intradermal, subcutaneous or intramuscular), intracranial, intrarenal, intraspinal, intrarectal or intravaginal. Depending on the condition being treated, one route may be preferred over others, which can be determined by those skilled in the art.

In other aspects of embodiments of the invention, a pharmaceutical composition comprising a therapeutic useful in anti-remodeling therapy, as disclosed herein, in a pharmaceutically-acceptable carrier, adjuvant or diluent is provided. For injection, the carrier will typically be a liquid. Pharmaceutically acceptable carriers, adjuvants and diluents are well-known to those skilled in the art and can contain the additives usual for injection solutions, such as stabilizing agents, salts or saline, and/or buffers.

In preferred embodiments, the compositions are formulated for parental administration. In other embodiments, the compositions are formulated as a sustained-release formulation.

In further preferred embodiments, the composition is released from at least one reservoir that is in operable communication with the processor of a processing system such that the administration of the therapy from the at least one reservoir is initiated from the processing device when the processing device performs the methods of embodiments of the invention. In some embodiments, the at least one reservoir and the processing device are integrated into the phonocardiogram recording device. In other embodiments, the processing device and the at least one therapy reservoir are integrated and located at a location separate from the phonocardiogram recording device.

In yet further embodiments, the phonocardiogram recording device, the at least one reservoir and the processing device are located in separate locations. In some embodiments, the phonocardiogram recording device is a digital stethoscope and the processing device is integrated into the stethoscope, whereas the at least one reservoir and the therapy administration device are operable communicating with, but located separate from, the stethoscope/processing device unit. In yet other embodiments, the processing device is in operable communication with, but not an integral part of, the stethoscope and the at least one reservoir and therapy administration device are in operable communication with the processing device and either integrated into or in separate location from the processing device.

In further embodiments, the methods and devices are used in the establishment of standardized heart sound parameters of heart valve performance and quantified coincidentally with imaging modalities to establish a combined sound feature-imaging feature library of heart valve conditions.

In other embodiments, the methods and devices are used in the establishment of standardized blood vessel sound parameters of blood vessel microstructure and performance and quantified coincidentally with imaging modalities to establish a combined sound feature-imaging feature library of blood vessel conditions.

The imaging modalities useful in embodiments of the subject invention include, but are not limited to, echocardiogram, ultrasound of blood vessels, magnetic resonance tomography and computer tomography of heart valves and blood vessels including, but limited to, aorta, carotid artery, iliac artery, femoral artery, and renal artery.

In some embodiments, the output of a combined sound feature-imaging feature analysis is a classification of heart sounds based on heart valve microstructure classification. In preferred embodiments, the combined sound feature-imaging feature analysis provides a heart valve classification into no stenosis/normal, mild stenosis, moderate stenosis, and severe stenosis. In further embodiments, the sound analysis parameters are combined with standard parameters of valve performance as measured by cardiac flow imaging using echocardiogram, functional MRI and/or functional CT.

In other some embodiments, the output of a combined sound feature-imaging feature analysis is a classification of blood vessel sounds based on blood vessel microstructure classification. In preferred embodiments, the combined sound feature-imaging feature analysis provides a blood vessel classification into no stenosis/normal, mild stenosis, moderate stenosis, and severe stenosis. In further embodiments, the sound analysis parameters are combined with standard parameters of blood vessel performance as measured by blood flow imaging using echocardiogram, functional MRI and/or functional CT.

In some embodiments, the methods and devices employ multivariant analysis to quantify sound characteristics. In further embodiments, the methods and devices employ machine learning using artificial neural networks to analyze and quantify sound characteristics.

Advantageously, the devices of embodiments of the invention can be used in connection with low-cost clinical tools, such as stethoscopes, and can be readily integrated into routine physical check-ups at a doctor's office.

The methods and devices of embodiments of the invention can be used on human and other species including, but not limited to, mice, rats, apes, chimpanzees, orangutans, monkey, dog, cat, guinea pig, hamster, rabbits, ferrets, cows, horses, goats and sheep.

Embodiments of the subject invention can also identify early stages of different valvular diseases, such as mitral regurgitation. For all valve diseases, tissue remodeling occurs before gross anatomical changes that alter valve and cardiac function. Embodiments of the subject invention can identify tissue microstructural changes of all four heart valves, as well as hemodynamic changes that affect the cardiac chambers and overall cardiac function. In order to correlate acoustic characteristics to the standard measures of valve and cardiac performance, embodiments of the subject invention not only correlate the acoustic properties to tissue biomechanics and microstructure, but also to functional parameters as measured by cardiac echocardiogram. Cardiac echocardiogram is the current standard to measure valve and cardiac function, which helps clinicians diagnose and monitor progression of disease. Using the current standard measures of disease, embodiments of the subject invention correlate stages of valvular and cardiac disease as measured by an echocardiogram to acoustic characteristics.

The methods and processes described herein can be embodied as code and/or data. The software code and data described herein can be stored on one or more machine-readable media (e.g., computer-readable media), which may include any device or medium that can store code and/or data for use by a computer system. When a computer system and/or processor and/or processing device of embodiments of the invention reads and executes the code and/or data stored on a computer-readable medium, the computer system and/or processor and/or processing device performs the methods and processes embodied as data structures and code stored within the computer-readable storage medium.

It should be appreciated by those skilled in the art that computer-readable media include removable and non-removable structures/devices that can be used for storage of information, such as computer-readable instructions, data structures, program modules, and other data used by a computing system/environment. A computer-readable medium includes, but is not limited to, volatile memory such as random access memories (RAM, DRAM, SRAM); and non-volatile memory such as flash memory, various read-only-memories (ROM, PROM, EPROM, EEPROM), magnetic and ferromagnetic/ferroelectric memories (MRAM, FeRAM), and magnetic and optical storage devices (hard drives, magnetic tape, CDs, DVDs); network devices; or other media now known or later developed that are capable of storing computer-readable information/data. Computer-readable media should not be construed or interpreted to include any propagating signals. A computer-readable medium of embodiments of the subject invention can be, for example, a compact disc (CD), digital video disc (DVD), flash memory device, volatile memory, or a hard disk drive (HDD), such as an external HDD or the HDD of a computing device, though embodiments are not limited thereto. A computing device can be, for example, a laptop computer, desktop computer, server, cell phone, or tablet, though embodiments are not limited thereto.

A greater understanding of the embodiments of the subject invention and of their many advantages may be had from the following examples, given by way of illustration. The following examples are illustrative of some of the methods, applications, embodiments, and variants of the present invention. They are, of course, not to be considered as limiting the invention. Numerous changes and modifications can be made with respect to the invention.

Example 1

Current modalities to diagnose CAVD rely on complex and costly imaging techniques. However, patients are generally asymptomatic during early CAVD when the remodeling may be treatable. It is unlikely that asymptomatic patients will be referred for these expensive imaging procedures. Embodiments of the subject invention provide low-cost techniques that only require the use of a staple clinical tool—the stethoscope. Therefore, the strategy can be easily implemented as part of routine physical check-ups. Additionally, therapeutic strategies to target cellular changes prior to late stages of valve remodeling already exist; however, none of these therapeutics can advance into a clinical trial stage since there are currently no means to diagnose CAVD at its early stages. Embodiments of the subject invention will advance research and clinical translation of therapeutics that treat heart valve remodeling.

Provided are methods and devices to identify microstructural differences in early aortic valve remodeling by detecting changes in the valve acoustic frequency (S2 sound)

response prior to traditional symptom manifestation of aortic valve disease. Using heart sound recordings obtained from a digital stethoscope, the frequency components of a signal were analyzed and related to stages of remodeling in the aortic valve. The frequency analysis was performed by doing a Fourier transform, which decomposes a time-domain signal into the frequency-domain. The frequency components of a heart sound change in respect to aortic valve health.

A digital stethoscope was used to record cardiac auscultations of a patient, a minimum of 3 cardiac cycles. Using an algorithm, the cardiac cycles were processed individually to analyze the frequency components. Several frequency analyses were performed on both heart sounds (S1 and S2), including a Fast Fourier Transform, Discrete Fourier Transform, and Short Time Fourier Transform. From these analyses, several features were used to assess the health of the aortic valve, included but not limited to amplitude spectrum, power spectral density, and the power/frequency (dB/Hz) of the signal. A combination of these features was used to assess the health of the aortic valve. Feature extraction and valve health assessment were correlated using an in vivo mouse model and in situ porcine studies.

Example 2

A segmentation method is used to label the first and second sound of a heart cycle. To this end, the sum of squares error between a classified region of Interest (ROI) that includes the cardiac cycle with first (S1) and second (S2) sounds is used to identify all cardiac cycles present in a signal and label S1 and S2 accordingly. From the digital phonocardiogram signal multiple characteristics are extracted, for example, dominant frequency components of S1 and S2 as determined by the Fast Fourier Transform (FFT) and Short-Time Fourier Transform (STFT); power spectral density; amplitude and shape (full-width half-max. lengths) of power spectral density of each heart sound (S1 and S2); intensity of S1 and S2 (Time); duration of S1 and S2 sound (TIME); diastole and systole duration (Time); presence of high frequency components (FFT and STFT); principal components of S1 and S2 as determined by principal component analysis.

Example 3

An algorithm that can detect frequency changes as a function of valve remodeling was developed in an in vivo mouse study. The algorithm has been translated for human use and is configured to be applied as an app or software. Heart sounds of a patient are uploaded from a commercially available digital stethoscope into the software. The algorithm performs a frequency analysis on the patient's heart sounds and identifies if the patient is at any stage of valve remodeling. The algorithm executed by a processing device is also implemented directly on a digital stethoscope, where the valve health assessment is directly computed and relayed onto the stethoscope itself, eliminating the need of any external software.

Example 4

Software was developed that uses machine learning to analyze heart sounds recorded from a commercially available stethoscope and provides an aortic valve health diagnostic. Sound was used because the second heart sound is predominantly created by the closure of the aortic valve and the second heart sound changes when the valve is severely diseased. Because no studies have assessed the earliest disease stages that could lead to changes in the sound, the instant method was developed to aid a physician when using a stethoscope during a clinical examination to detect and quantify sound modifications that indicate early microstructural changes in the aortic valve and allows early treatment of microstructural valve changes. Using a commercially available stethoscope, heart sounds are recorded and uploaded into the software of embodiments of the invention. The software performs a real time analysis of the frequency and time characteristics of the heart sound. These characteristics are used to measure the presence and stage of aortic valve disease. This procedure can easily be implemented in a routine visit to the doctor and allows early detection and treatment of patient with aortic valve disorders.

It should be understood that the examples and embodiments described herein are for illustrative purposes only and that various modifications or changes in light thereof will be suggested to persons skilled in the art and are to be included within the spirit and purview of this application.

All patents, patent applications, provisional applications, and publications referred to or cited herein are incorporated by reference in their entirety, including all figures and tables, to the extent they are not inconsistent with the explicit teachings of this specification.

What is claimed is:

1. A method for processing at least one heart sound signal to detect and quantify heart valve remodeling, the method comprising:
    measuring, using a phonocardiogram recording device, at least one heart sound signal to give a phonocardiogram;
    segmenting the at least one heart sound signal into a plurality of segments;
    extracting acoustic features from the plurality of segments;
    performing an unsupervised machine learning process on the acoustic features to classify the at least one heart sound signal according to a level of heart valve remodeling, thereby detecting and quantifying heart valve remodeling from the at least one heart sound signal; and
    administering to a subject, from which the at least one heart sound signal is measured, an anti-remodeling therapy if at least one acoustic feature of the at least one heart sound signal deviates from a respective predetermined acoustic feature value,
    the anti-remodeling therapy comprising administering to the subject at least one of an angiotensin-converting enzyme inhibitor, an angiotensin-converting enzyme blocker, an IL-6 antibody, a small molecule ACE inhibitor, a small molecule IL-6 inhibitor, an inhibitor of metalloproteinases, an inhibitors of leukotriene B4, an inhibitor of TGF-beta1, an inhibitor of cytokines, TGF-$\beta$1, IL-10, INF-$\gamma$, INF-$\lambda$, and a nonsteroidal anti-inflammatory drug (NSAID).

2. The method according to claim 1, the extracting of acoustic features comprising identifying eigenvalues of the at least one heart sound signal using eigenvectors determined by principal component analysis of an entire heart sound database.

3. The method according to claim 2, the performing of the unsupervised machine learning process comprising clustering eigenvalues for a corresponding number of eigenvectors using a k-means clustering algorithm.

4. The method according to claim 1, the segmenting of the at least one heart sound signal comprising:

selecting a region of interest (ROI) from the phonocardiogram;

calculating, by a processor in operable communication with the phonocardiogram recording device, a sum of squares error between envelopes of the ROI and remaining sound signals recorded in the phonocardiogram; and selecting a location of a cardiac cycle present in the at least one heart sound signal.

5. The method according to claim 1, the extracting of acoustic features comprising at least one of:
   a) measuring temporal and spectral features of the plurality of segments in real time;
   b) measuring frequencies of the plurality of segments and calculating a dominant frequency of the plurality of segments using at least one of Fast Fourier Transform and Short-Time Fourier Transform; and
   c) measuring a power spectral density of the plurality of segments.

6. The method according to claim 1, the extracting of acoustic features comprising:
   measuring a power spectral density of the plurality of segments; and
   at least one of the following:
   i) measuring an amplitude and a shape of the power spectral density of the plurality of segments; and
   ii) measuring an area under a curve for the power spectral density of the plurality of segments.

7. The method according to claim 1, the performing of the unsupervised machine learning process comprising correlating heart sound features of the at least one heart sound signal as determined in temporal, frequency, and unsupervised learning analyses to stages of disease as measured by cardiac echocardiogram parameters and tissue properties.

8. A method for processing at least one heart sound signal to detect and quantify heart valve remodeling, the method comprising:
   measuring, using a phonocardiogram recording device, at least one heart sound signal to give a phonocardiogram;
   segmenting the at least one heart sound signal into a plurality of segments; and
   extracting acoustic features from the plurality of segments; and
   performing an unsupervised machine learning process on the acoustic features to classify the at least one heart sound signal according to a level of heart valve remodeling, thereby detecting and quantifying heart valve remodeling from the at least one heart sound signal,
   the segmenting of the at least one heart sound signal comprising:
   selecting a region of interest (ROI) from the phonocardiogram;
   calculating, by a processor in operable communication with the phonocardiogram recording device, a sum of squares error between envelopes of the ROI and remaining sound signals recorded in the phonocardiogram; and
   selecting a location of a cardiac cycle present in the at least one heart sound signal,
   the extracting of acoustic features comprising at least one of:
   a) measuring temporal and spectral features of the plurality of segments in real time;
   b) measuring frequencies of the plurality of segments and calculating a dominant frequency of the plurality of segments using at least one of Fast Fourier Transform and Short-Time Fourier Transform; and
   c) measuring a power spectral density of the plurality of segments, followed by measuring an amplitude and a shape of the power spectral density and measuring an area under a curve for the power spectral density,
   the extracting of acoustic features comprising identifying eigenvalues of the at least one heart sound signal using eigenvectors determined by principal component analysis of an entire heart sound database,
   the performing of the unsupervised machine learning process comprising clustering eigenvalues for a corresponding number of eigenvectors using a k-means clustering algorithm,
   the performing of the unsupervised machine learning process comprising correlating heart sound features of the at least one heart sound signal as determined in temporal, frequency, and unsupervised learning analyses to stages of disease as measured by cardiac echocardiogram parameters and tissue properties,
   the method further comprising administering to a subject, from which the at least one heart sound signal is measured, an anti-remodeling therapy if at least one acoustic feature of the at least one heart sound signal deviates from a respective predetermined acoustic feature value, and
   the anti-remodeling therapy comprising administering to the subject at least one of an angiotensin-converting enzyme inhibitor, an angiotensin-converting enzyme blocker, an IL-6 antibody, a small molecule ACE inhibitor, a small molecule IL-6 inhibitor, an inhibitor of metalloproteinases, an inhibitors of leukotriene B4, an inhibitor of TGF-beta1, an inhibitor of cytokines, TGF-$\beta$1, IL-10, INF-$\gamma$, INF-$\lambda$, and a nonsteroidal anti-inflammatory drug (NSAID).

* * * * *